US012626799B2

(12) United States Patent
Master et al.

(10) Patent No.: US 12,626,799 B2
(45) Date of Patent: May 12, 2026

(54) SYSTEMS AND METHODS FOR WEAKLY-SUPERVISED REPORTABILITY AND CONTEXT PREDICTION, AND FOR MULTI-MODAL RISK IDENTIFICATION FOR PATIENT POPULATIONS

(71) Applicant: SQ Care Management, LLC, Overland Park, KS (US)

(72) Inventors: Neel Master, Framingham, MA (US); Joseph Max Kaufmann, Framingham, MA (US); Michael Alan Nossal, Framingham, MA (US); Jennifer O. Clarke, Framingham, MA (US); David Andrew Miller, Framingham, MA (US); Maren Beus, Framingham, MA (US); Amit Patel, Framingham, MA (US)

(73) Assignee: SQ Care Management, LLC, Overland Park, KS (US)

( * ) Notice: Subject to any disclaimer, the term of this patent is extended or adjusted under 35 U.S.C. 154(b) by 441 days.

(21) Appl. No.: 17/882,179

(22) Filed: Aug. 5, 2022

(65) Prior Publication Data

US 2023/0125785 A1 Apr. 27, 2023

Related U.S. Application Data

(60) Provisional application No. 63/272,074, filed on Oct. 26, 2021.

(51) Int. Cl.
| | |
|---|---|
| *G16H 20/00* | (2018.01) |
| *G06F 40/295* | (2020.01) |
| *G16H 10/60* | (2018.01) |
| *G16H 15/00* | (2018.01) |
| *G16H 50/20* | (2018.01) |

(52) U.S. Cl.
CPC .......... *G16H 20/00* (2018.01); *G06F 40/295* (2020.01); *G16H 10/60* (2018.01); *G16H 15/00* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 2006/0289020 | A1* | 12/2006 | Tabak .................. | A61B 5/4833 |
| | | | | 702/19 |
| 2009/0177493 | A1* | 7/2009 | Narayan ................ | G06Q 10/10 |
| | | | | 705/3 |

(Continued)

OTHER PUBLICATIONS

Sanyal, Josh, "Weakly supervised temporal model for prediction of breast cancer distant recurrence," Scientific Reports (2021) 11: 9461, May 4, 2021 (Year: 2021).*

*Primary Examiner* — John P Go

(74) *Attorney, Agent, or Firm* — Erise IP, P.A.

(57) ABSTRACT

Presented herein are systems and methods for automated analysis of patient data. More particularly, in certain embodiments, the invention relates to systems and methods for predicting the context of a particular phrase (e.g. the name of a diagnosis/condition) in a clinical record of a patient using a reportability classifier. In another aspect, the invention relates to systems and methods for automatically identifying a potential care gap and/or adverse health trend for a patient from clinical data.

68 Claims, 6 Drawing Sheets

300

(56) References Cited

U.S. PATENT DOCUMENTS

| | | | |
|---|---|---|---|
| 2009/0299977 A1* | 12/2009 | Rosales | G16H 10/60 |
| 2015/0095016 A1* | 4/2015 | Karres | G16H 10/20 |
| | | | 704/9 |
| 2015/0149215 A1* | 5/2015 | Qian | G06F 16/335 |
| | | | 705/3 |
| 2016/0358284 A1* | 12/2016 | Bagley | G16H 10/60 |
| 2018/0350459 A1* | 12/2018 | Yang | G06N 3/045 |
| 2019/0057774 A1* | 2/2019 | Velez | G16H 50/20 |
| 2020/0118682 A1* | 4/2020 | Villazón-Terrazas | |
| | | | G06N 20/00 |
| 2020/0193153 A1* | 6/2020 | Lee | G06F 40/226 |
| 2021/0225470 A1* | 7/2021 | Elliott | G16H 10/60 |
| 2021/0343410 A1* | 11/2021 | Zhang | G06F 16/285 |
| 2021/0350884 A1* | 11/2021 | Weikert | G16H 15/00 |
| 2021/0374334 A1* | 12/2021 | Li | G06N 20/00 |
| 2021/0406739 A1* | 12/2021 | O'Connor | G06N 3/08 |

* cited by examiner

100

200

202

Receiving and/or accessing a problem list of the patient and the clinical record of the patient

204

Identifying one or more named entity phrases in the text of the clinical record

206

Classifying at least one of the one or more named entity phrases

208

Mapping entity phrases to diagnostic codes using a code classifier

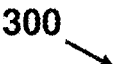

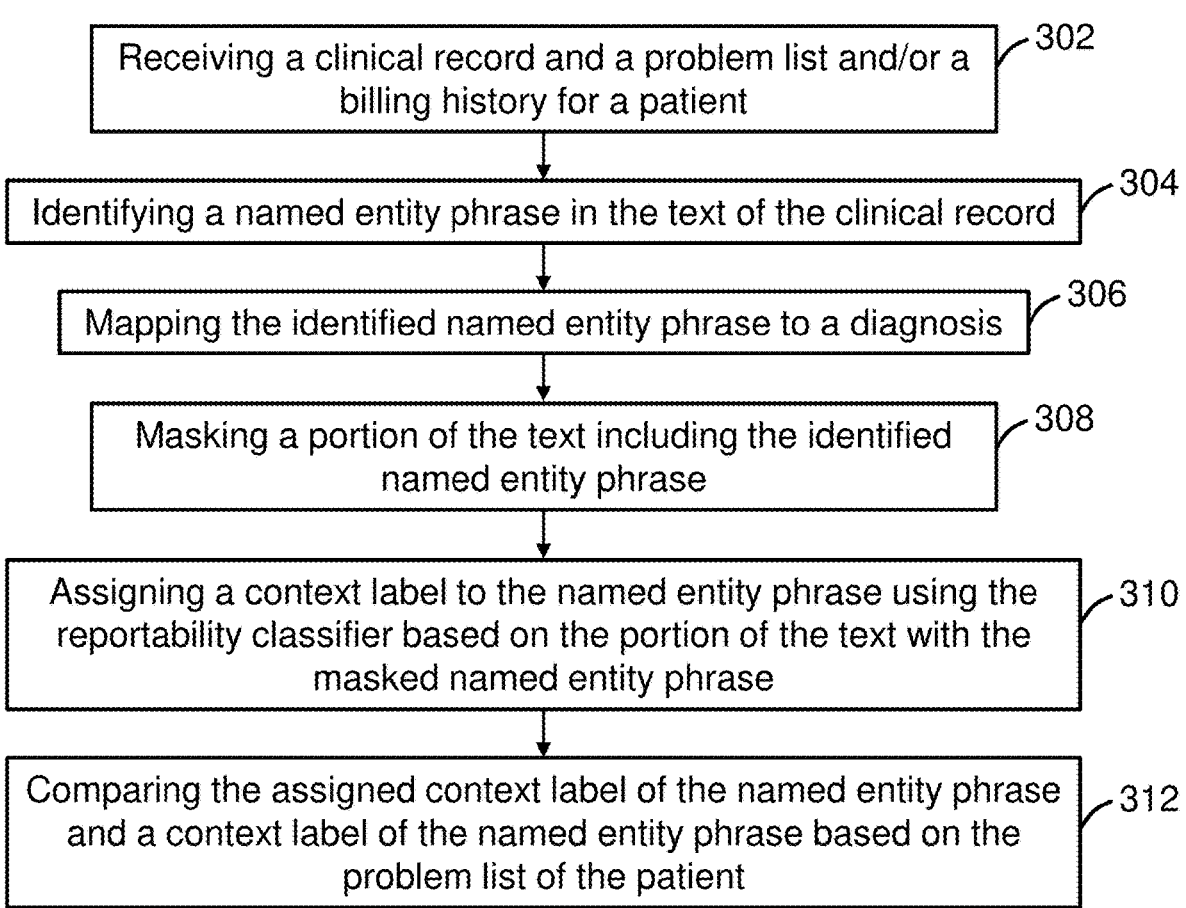

Receiving a clinical record and a problem list and/or a billing history for a patient ⌐302

Identifying a named entity phrase in the text of the clinical record ⌐304

Mapping the identified named entity phrase to a diagnosis ⌐306

Masking a portion of the text including the identified named entity phrase ⌐308

Assigning a context label to the named entity phrase using the reportability classifier based on the portion of the text with the masked named entity phrase ⌐310

Comparing the assigned context label of the named entity phrase and a context label of the named entity phrase based on the problem list of the patient ⌐312

402
Receiving clinical data related to the patient

404
Using a rule-based algorithm and/or a machine learning algorithm

406
Automatically identifying a potential care gap and/or an adverse health trend for the patient from the clinical data

500

SYSTEMS AND METHODS FOR WEAKLY-SUPERVISED REPORTABILITY AND CONTEXT PREDICTION, AND FOR MULTI-MODAL RISK IDENTIFICATION FOR PATIENT POPULATIONS

CROSS-REFERENCE TO RELATED APPLICATION

This application claims the benefit of and priority to U.S. Provisional Application No. 63/272,074, filed Oct. 26, 2021, entitled "Systems and Methods for Weakly-Supervised Reportability and Context Prediction, and for Multi-Modal Risk Identification for Patient Populations," the contents of which is hereby incorporated by reference in its entirety.

FIELD

This invention relates generally to systems and methods for automated analysis of patient clinical data.

BACKGROUND

Patients have a wide variety of clinical data associated with their care, arising from diverse sources including diagnostic test results from different labs and narrative notes from different practitioners. The use of digital tools such as medical records, digitized lab reporting, and digital dictations provides electronic sources of clinical data that can be very effective at conveying a significant range of information related to patient care. While managing, analyzing, and tracking this clinical data is important to properly coordinate treatments and care for the patient, especially for chronic care management, it is challenging for patients and their caregivers to do so using the currently available tools.

Accordingly, there exists a need for systems and methods which efficiently and effectively interpret clinical data.

SUMMARY

Presented herein are systems and methods for automated analysis of patient data. More particularly, in certain embodiments, the invention relates to systems and methods for predicting the context of a particular phrase (e.g. the name of a diagnosis/condition) in a clinical record of a patient using a reportability classifier. In certain embodiments, the reportability classifier comprises a deep-learning algorithm. A masking technique presented herein improves the performance of the reportability classifier.

In another aspect, the invention relates to systems and methods for automatically identifying a potential care gap and/or an adverse health trend for a patient from clinical data. This involves integration of machine learning into the workflow in the context of care coordination to identify, confirm, and close care gaps and provide suggested actions for maintaining the patient's overall health. For example, techniques are presented for updating the machine learning algorithm with feedback received from a triggered human review, e.g., wherein the feedback received from the triggered human review is used as training data for an update of the machine learning algorithm.

In one aspect, the invention is directed to a method for automatically assigning a context label to each of one or more named entity phrases from a clinical record of a patient, the method comprising: receiving and/or accessing, by a processor of a computing device, a clinical record (e.g., a document comprising clinical dictation) of a patient;

automatically identifying, by the processor, one or more named entity phrases in the clinical record of the patient; and automatically assigning, by the processor, a context label to each of the one or more named entity phrases by using a reportability classifier.

In certain embodiments, the one or more named entity phrases comprises a diagnosis, a disease, a condition, a clinical entity, or an International Classification of Diseases code (e.g., ICD-10).

In certain embodiments, the context label comprises a label corresponding to a member selected from the group consisting of: "not reportable", "clinical finding", family history", or "personal history".

In certain embodiments, the method comprises receiving a problem list corresponding to the patient. In certain embodiments, the problem list comprises a combination of one or more of: an illness, an injury, a diagnosis, a condition, and a social problem. In certain embodiments, problem list comprises one or more diagnoses (e.g., current and/or resolved diagnoses).

In certain embodiments, the method comprises automatically triggering a human review workflow (e.g., a workflow that, upon confirmation, automatically notifies a care team or care individual assigned to the patient of a discrepancy) based on the context label of said named entity phrase. In certain embodiments, the method comprises adding a problem, removing the problem, or updating a status of the problem in the problem list (e.g., identifying if a problem is resolved, inactive, active, improving, or worsening) following feedback received from the triggered human review.

In certain embodiments, the method comprises updating the reportability classifier with feedback received from the triggered human review. In certain embodiments, the reportability classifier comprises a deep-learning algorithm. In certain embodiments, the feedback received from the triggered human review is used as training data for an update of the reportability classifier. In certain embodiments, the training data further comprises data from the clinical record (e.g., the EMR) of the patient.

In certain embodiments, the method comprises identifying, by the processor, (e.g., using a machine learning algorithm) a problem corresponding to the patient (e.g., a problem not identified in the clinical record of the patient) based on the one or more automatically identified named entity phrases and the corresponding context labels of said named entity phrases.

In certain embodiments, the method comprises determining, by the processor, whether each of the one or more named entity phrases is a negated concept (e.g., determining whether or not the problem is reportable, e.g., if the named entity phrase relates to a family member) by using the reportability classifier.

In certain embodiments, the method comprises automatically identifying (e.g., by the processor) a care gap using the problem list. In certain embodiments, automatically identifying the care gap comprises identifying a therapy and/or a treatment the patient could be receiving but is not currently receiving. In certain embodiments, automatically identifying the care gap comprises recommending a therapy (e.g., a medication and/or treatment) using the problem list.

In certain embodiments, the clinical record is an electronic medical record (EMR).

In certain embodiments, the clinical record comprises unstructured data. In certain embodiments, the unstructured data comprises clinical dictation, clinical notes, and/or clinical reports. In certain embodiments, the unstructured data comprises one or more strings of alphanumeric characters (e.g., natural language text).

In certain embodiments, the clinical record comprises laboratory results of the patient, patient vitals, patient demographics, patient problems, patient medications, clinical notes, clinical dictation, clinical reports, and/or past medical history.

In certain embodiments, the method does not require receiving or accessing an encounter document comprising billable codes (e.g., ICD codes) corresponding to the patient.

In certain embodiments, the named entity phrase is a disease or a condition (e.g., a symptom, a complaint, a lab result, an abnormal finding (e.g., an abnormal test result), or a social circumstance (e.g., homelessness).

In certain embodiments, the method comprises automatically mapping, by the processor, each of the one or more named entities to a corresponding ontological code (e.g., a code corresponding to a diagnosis or condition) by using a first code classifier (e.g., a pattern and edit distance approach to map from a phrase to a Unified Medical Language System (UMLS) concept) (e.g., QuickUMLS)). In certain embodiments, the ontological code corresponds to a Unified Medical Language System (UMLS) code, an International Classification of Diseases (ICD) code (e.g., ICD10 code), or an RxNorm Normalized Names (RXNORM) code. In certain embodiments, the one or more ontological codes are high level codes that are specific to a general disease or condition. In certain embodiments, the method comprises updating each of the one or more ontological codes (e.g., made more specific) by using a second code classifier to make the one or more ontological codes more specific. In certain embodiments, the first and/or second code classifiers is/are deeplearning algorithms (e.g., a deep-learning algorithm that leverages a small amount of human annotated data within an active learning framework that identifies training examples with high uncertainty for human review).

In certain embodiments, the reportability classifier comprises a deep-learning algorithm.

In certain embodiments, the reportability classifier comprises a neural network (e.g., a recurrent neural network (RNN)).

In certain embodiments, the reportability classifier comprises a bidirectional long short-term memory (LSTM) network.

In certain embodiments, the reportability classifier is a trained model, having been trained using a training dataset to determine the context labels (e.g., not reportable, clinical finding, family history, personal history) of named entity phrases (e.g., diagnoses) in medical records of one or more patients (e.g., based on a string of text (e.g., sentences, phrases, etc.) containing said named entity phrases).

In certain embodiments, the training dataset comprises a weakly-labeled training dataset.

In certain embodiments, the training dataset comprises one or more (e.g., a plurality of) clinical records (e.g., documents comprising clinical dictation, clinical notes) comprising unstructured data (e.g., unstructured text data) from each of the one or more (e.g., a plurality of) patients, wherein each of the one or more (e.g., the plurality of) clinical records comprises a named entity phrase (e.g., a labeled named entity phrase).

In certain embodiments, the training dataset does not include billing codes (e.g., specific ICD codes).

In certain embodiments, the training dataset comprises clinical dictation and/or clinical notes for each of the one or more patients.

In certain embodiments, the training data set comprises a problem list for each of the patients.

In certain embodiments, the reportability classifier has been trained by masking the named entity phrase in text (e.g., a string of text) of the medical record and classifying an unmasked portion of the text containing said named entity phrase with the context label, wherein the context label is based on, at least, the presence or absence of said named entity in the problem list of the patient.

In certain embodiments, the second code classifier is a trained model, having been trained using a code training dataset (e.g., a labeled code training dataset) to determine a specific ontological code (e.g., diabetes with hyperglycemia) corresponding to named entity phrases (e.g., diagnoses) comprising a plurality of patient examples corresponding to the specific ontological code. In certain embodiments, the plurality of patient examples comprises at least 10 patient examples of the specific ontological code. In certain embodiments, the plurality of patient samples comprises between about 10 and about 25 patient examples of the specific ontological code. In certain embodiments, each of the patient examples comprises a clinical record (e.g., clinical dictation) comprising the named entity.

In certain embodiments, the method comprises automatically identifying, by the processor, one or more drugs in the clinical record of the patient. In certain embodiments, the method comprises mapping, by the processor, at least one of the one or more drugs to a problem (e.g., a disease or condition). In certain embodiments, the method comprises updating the problem list of the patient with the mapped problem.

In another aspect, the invention is directed to a system for automatically assigning a context label to named entity phrases (e.g., diagnoses) from a clinical record (e.g., an electronic record) of a patient, the system comprising: a processor; and a memory having instructions stored thereon, wherein the instructions, when executed by the processor, cause the processor to perform a method described herein.

In another aspect, the invention is directed to a method for automatically identifying diagnostic codes using a clinical record of a patient, the method comprising: receiving and/or accessing, by a processor of a computing device, a problem list of the patient (e.g., a list comprising conditions, diagnoses, diseases) and the clinical record (e.g., clinical notes, clinical dictation) of the patient, wherein the clinical record comprises text (e.g., unstructured text); automatically identifying, by the processor, one or more named entity phrases in the text of the clinical record; automatically classifying, by the processor, at least one of the one or more named entity phrases as reportable (e.g., a clinical entity, e.g., a diagnosis, a condition) in the clinical record of the patient by using a reportability classifier, wherein the classification of the one or more named entity phrases is based on, at least, the context of (e.g., one or more words of the text other than the at least one named entity phrase) the at least one named entity phrase and the problem list of the patient; and automatically mapping, by the processor, the at least one of the reportable named entity phrases to a diagnostic code (e.g., a Unified Medical Language System (UMLS) code, an International Classification of Diseases (ICD) code (e.g., ICD10 code), or an RxNorm Normalized Names (RXNORM) code) by using a code classifier, wherein the code corresponds to a diagnosis.

In another aspect, the invention is directed to a method of training a reportability classifier (e.g., a deep learning algorithm, e.g., an artificial neural network) to assign a context label to a named entity phrase in a clinical record of a patient, the method comprising: receiving, by a processor of a computing device, (i) a clinical record (e.g., clinical notes, e.g., unstructured text) and (ii) a problem list and/or a billing history for a patient, wherein the clinical record comprises text (e.g., unstructured text); identifying, by the processor, a named entity phrase in the text of the clinical record; mapping, by the processor, the identified named entity phrase to a diagnosis; masking, by the processor, a portion of the text comprising the identified named entity phrase; assigning, by the processor, a context label to the named entity phrase using the reportability classifier based on the portion of the text comprising the masked named entity phrase; and comparing, by the processor, the assigned context label of the named entity phrase and a context label of the named entity phrase based on, at least, the problem list of the patient.

In certain embodiments, mapping the named entity phrase to the diagnosis is performed using a diagnostic classifier (e.g., a deep learning algorithm). In certain embodiments, the diagnostic classifier comprises a machine learning algorithm.

In certain embodiments, mapping the named entity phrase to the diagnosis comprises mapping the named entity phrase to a diagnostic code (e.g., an International Classification of Diseases (ICD) code).

In certain embodiments, the masked portion of the text comprises, at least, the named entity phrase.

In certain embodiments, the reportability classifier is a neural network (e.g., a recurrent neural network (RNN), e.g., a bidirectional long short-term memory (LSTM) network).

In certain embodiments, the reportability classifier comprises a member selected from the group consisting of Long short term memory (LSTM), Bilateral LSTM (BiLSTM), Embeddings from Language Models (Elmo), Bidirectional Encoder Representations (BERT), Bert trained on clinical notes (Clinical BERT), Distilled BERT (DistilBERT), and A Lite BERT (AlBERT).

In certain embodiments, the method does not require receiving an encounter document (e.g., a document comprising billable codes) of the patient.

In certain embodiments, the method does not require receiving one or more billable codes corresponding to a disease or a condition of the patient.

In certain embodiments, the clinical record comprises clinical notes and/or clinical dictation.

In certain embodiments, the clinical record comprises unstructured text.

In certain embodiments, the context label is indicative of whether or not the named entity phrase is reportable (e.g., wherein the named entity phrase is indicative that the named entity phrase currently applies to the subject).

In another aspect, the invention is directed to a method for automatically identifying a potential care gap and/or an adverse health trend for a patient, the method comprising: receiving and/or accessing, by a processor of a computing device, clinical data (e.g., structured clinical data) related to the patient (e.g., one or more members selected from the group consisting of electronic health record data, physician notes, data from a monitoring device, self-reported patient data, billing data, laboratory data, data from a patient vial, and external source data); and automatically identifying, by the processor, the potential care gap and/or adverse health trend for the patient from the clinical data using a rule-based algorithm and/or a machine learning algorithm.

In certain embodiments, the machine learning algorithm comprises natural language processing (NLP) software [e.g., Long short term memory (LSTM), Bilateral LSTM (BiL- STM), Embeddings from Language Models (Elmo), Bidirectional Encoder Representations (BERT), Bert trained on clinical notes (Clinical BERT), Distilled BERT (DistilBERT), and/or A Lite BERT (AlBERT)].

In certain embodiments, the method further comprises automatically triggering a human review workflow wherein a care team or care individual assigned to the patient is notified of a finding of a potential care gap and/or potential adverse health trend for the patient.

In certain embodiments, method further comprises updating the machine learning algorithm by using feedback received from the triggered human review as training data for the update of the machine learning algorithm. In certain embodiments, the training data further comprises data from a clinical record (e.g., an EMR) of the patient.

In certain embodiments, the clinical data is structured using a method as described herein.

In certain embodiments, the clinical data related to the patient comprises a healthcare provider narrative that references a medication indicating a condition that is missing from an electronic health record of the patient, thereby triggering a human review workflow (e.g., a workflow to trigger human review of the patient's health record for possible correction).

In certain embodiments, automatically identifying the potential care gap and/or adverse health trend comprises a member selected from the group consisting of: (i) determining whether a HEDIS-defined (Healthcare Effectiveness Data and Information Set) intervention applies for the patient, (ii) tracking changes in one or more vital signs for the patient (e.g., from a wearable sensing device) over time and alerting a care navigator for the patient of a potential adverse health trend based on the tracked changes, (iii) identifying a change in medication prescribed and/or taken by the patient and alerting a care navigator for the patient of the change, (iv) identifying that the patient may not be following a prescribed protocol or initiative and alerting a care navigator for the patient accordingly, and (v) monitoring data from a remote monitoring program and alerting a care navigator for the patient in the event of an anomalous reading.

In another aspect, the invention is directed to a system for automatically identifying a potential care gap and/or adverse health trend for a patient, the system comprising: a processor; and a memory having instructions stored thereon, wherein the instructions, when executed by the processor, cause the processor to perform a method as described herein.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 3 is a flowchart showing a method of training a reportability classifier to assign a context label to a named entity phrase in a clinical record of a patient, according to an illustrative embodiment.

Figure 1:
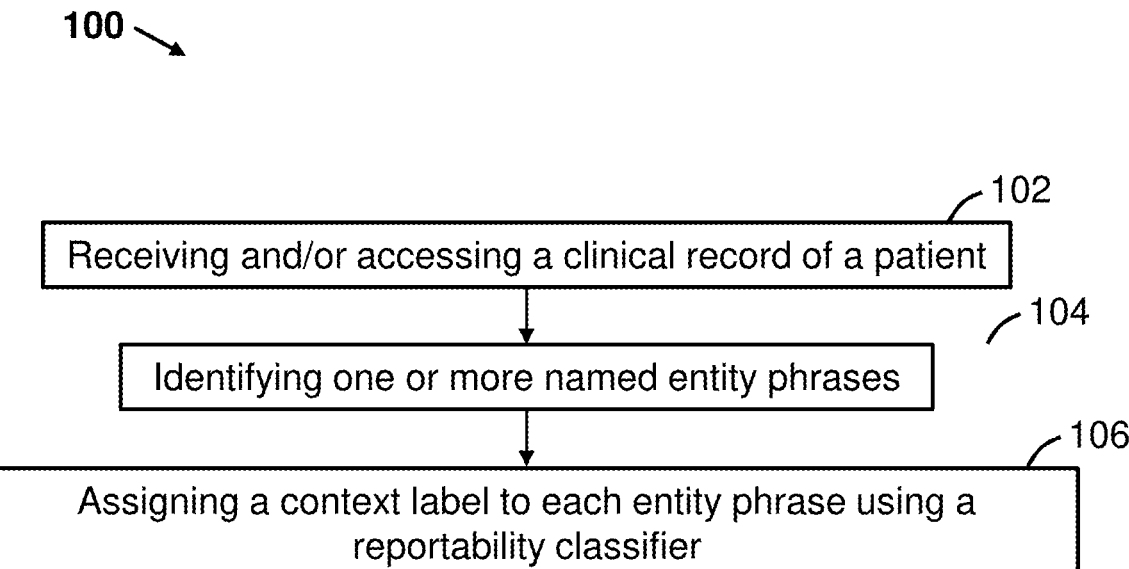
FIG. 1 is a flowchart showing a method for automatically assigning a context label to entity phrases from a clinical record, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Code: As used herein, the term "code" typically refers to a standardized alphanumeric string. In certain embodiments, a code used to represent a specific health condition (e.g., a diagnosis) or treatment. In certain embodiments, codes are used by medical practitioners and/or insurance payers. In certain embodiments, a code may be a Unified Medical Language System (UMLS) code, an International Classification of Diseases (ICD) code (e.g., ICD10 code), or an RxNorm Normalized Names (RXNORM) code.

Electronic health record (EHR) and electronic medical record (EMR): As used herein, the terms "electronic health record (EHR)" and "electronic medical record (EMR)" are used interchangeably to refer to collections of health information stored electronically.

Patient: As used herein, the term "patient" or "subject" are used interchangeably to refer to any individual which is being monitored (e.g., actively or passively monitored) by a provider (e.g., a healthcare provider) using the methods and systems described herein. In certain embodiments, a patient is an individual who is provided a treatment is or may be administered a treatment, e.g., for experimental, diagnostic, prophylactic, cosmetic, and/or therapeutic purposes. In some embodiments, a patient is a human. In some embodiments, a patient is suffering from or susceptible to one or more disorders or conditions. In some embodiments, a patient displays one or more symptoms of a disorder or condition. In some embodiments, a patient does not display symptoms of a disorder or condition. In some embodiments, a patient has been diagnosed with one or more disorders or conditions. In some embodiments, the patient is receiving or has received certain therapy to diagnose and/or to treat a disease, disorder, or condition.

Treatment: As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. Thus, in some embodiments, treatment may be prophylactic; in some embodiments, treatment may be therapeutic.

Wearable sensing device: As used herein, the term "wearable sensing device" refers to an electronic device that is worn by an individual (e.g., a patient) to measure and record health data of the patient. In certain embodiments, wearable sensing devices include smartwatches, wearable electrocardiography (ECG) devices, wearable meters (e.g., glucose meters), and the like. Examples of data that can be monitored (e.g., collected) by a wearable device includes, but is not limited to, heart rate, sleep cycles, steps walked, levels of activity, and breathing rate.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Weak supervision is a branch of machine learning where noisy, limited, or imprecise sources are used to provide a supervision signal for labeling large amounts of training data in a supervised learning setting. This approach alleviates the burden of obtaining hand-labeled data sets, which can be costly or impractical. Instead, inexpensive weak labels are employed with the understanding that they are imperfect, but can nonetheless be used to create a strong predictive model.

A natural language processing analysis of clinical dictation may see a phrase indicating a problem or condition, but whether this indicates that the patient actually has the condition requires an understanding of the context in which the phrase is used. In certain embodiments, systems and methods described herein predict whether a diagnosis (e.g., mapped to the ICD codeset, i.e., International Classification of Diseases, e.g., ICD-10, Tenth Revision) that is identified in a clinical record (e.g., an electronic medical record, EMR) of a patient indicates that the patient has the identified condition, refers to a family member or past incident, or is otherwise "not reportable". This determination is made by a reportability classifier, which may include a machine learning (e.g., deep-learning) algorithm and/or one or more rule based algorithms.

In certain embodiments, the reportability classifier assigns a context label to a named entity phrase in a clinical record of a patient that is associated with a code (e.g., an ICD code). In certain embodiments, the reportability classifier assigns one of the following context labels to each named entity phrase in a clinical record of a patient that is associated with an ICD10 code: (i) Not Reportable, (ii) Clinical Finding, (iii) Family History, or (iv) Personal History. In the case that the family history or personal history code is predicted, then the ICD10 code is translated (e.g., transformed) into the appropriate "Family History" or "Personal History" ICD10 "z-code". Z-codes are a special group of codes provided in ICD-10-CM for the reporting of factors influencing health status and contact with health services. In certain embodiments, z-codes are used to document social determinants of health. In certain embodiments, z-codes relate to housing, food security (or food insecurity), and transportation. If "Not Reportable" is predicted, then the ICD10 code would frequently be ignored in workflows triggered by a patient having that code.

The reportability classifier may identify whether the named entity phrase is used in a negated or equivocal clinical context, or refers to a past or future event. This may involve application of set rules, and/or it may involve use of a machine learning algorithm, e.g., natural language processing (NLP). Distant supervision may be used, for example, as the learning scheme to train the machine learning algorithm with a weakly labeled training data set.

In certain embodiments, the reportability classifier comprises a machine learning algorithm adapted to this clinical application by customization of the feature function and objective function.

The feature function may take (e.g., as input) a phrase that has been mapped to a diagnosis. It is presently found to be particularly beneficial to mask the content of the word or phrase that is mapped to the diagnosis so that the machine learning (ML) algorithm is forced to key off the surrounding text. For example, in the sentence, "The patient's diabetes remains steady," the ML engine is able to detect "diabetes" as a clinical phrase mapped to non-billable ICD10 code Ell ("DM type 2"). Masking the word "diabetes" yields features: "The patient's <diagnosis> remains steady."

In certain embodiments, the objective function assigns a label to training examples. For example, to do so, a terminology service is referenced, which associates Ell with Unified Medical Language System (UMLS) concepts for "diabetes" and "current condition" contexts. If the patient's problem list contains a more specific billable ICD10 that is also associated with diabetes, then the "CURRENT_PROBLEM" label is assigned. If instead, the problem list contains no diabetes related codes other than "family history of diabetes" (Z83.3) then "FAMILY_HISTORY" is assigned. Otherwise the "NON_REPORTABLE" label is assigned.

In this example, a patient's problem list and clinical text are both leveraged, even though there are no linkages to say that a given document contains any of the specific codes (e.g., ICD10 codes) listed in the problem list. Most EMRs have specific encounter documents associated with a code used to bill that specific encounter. However, this data may be unavailable and/or not otherwise provided as part of the clinical record document(s) provided. Moreover, a primary interest is determining whether a patient has a particular condition, rather than whether a particular condition can be used for billing purposes. In certain embodiments, the patient's clinical narrative is leveraged to correct the patient's problem list, so that the patient can be appropriately treated for all of their conditions/health problems.

In certain embodiments, a clinical narrative includes details on an interaction between a provided and a patient. In certain embodiments, a clinical narrative may include details of a patient (e.g., age, sex, weight), clinical condition of a patient, condition or disease being treated, treatments recommended and/or administered, laboratory measurements, and/or other findings.

Furthermore, it is desirable for the algorithm to "learn" the context phrases that indicate a family history context, regardless of whether the family history code for that condition occurs in the training set. By masking the content of the diagnosis, the ML model is encouraged to learn, for example, that a diagnosis following "mother had" indicates a family history context.

A reportability classifier implementing the aforementioned masking technique works surprisingly well. A trial scored by a human annotator indicated the accuracy of an implementation of the reportability classifier (e.g., when assigning context labels) is greater than 90%.

In another aspect, described herein is a system for multimodal risk identification, prediction, and care management of patient populations at-scale. For example, described is a system that supports automated identification of potential care gaps and adverse health trends for individual patients. These findings are presented to a patient care coordinator for confirmation with the patient. In certain embodiments, the findings are presented along with the context of the findings, customizable recommended actions, including establishing and tracking goals with the patient, and manual and automated interventions to the patient's care team to maintain and measure overall patient health and effective use of healthcare spend.

Automated identification is based on data and trends in patient self-reported data and a patient's electronic health record, including physician notes, monitoring devices (e.g., wearable monitoring devices), and external sources. The system includes a feedback loop that utilizes machine learning to improve overall identification over time.

In certain embodiments, clinical data (e.g., structured clinical data) related to the patient is received or accessed. The clinical data may include, for example, electronic health record data, physician notes, data from a monitoring device, self-reported patient data, billing data, laboratory data, data from patient vitals, and/or external source data. A potential care gap and/or adverse health trend for the patient is then automatically identified from the clinical data using a ML algorithm, for example, natural language processing (NLP) software. In certain embodiments, human review (e.g., a human review workflow) is automatically triggered if a potential care gap or adverse health trend is identified. In certain embodiments, the ML algorithm is updated with feedback received from the triggered human review, e.g., the human feedback is used as training data for an update of the machine learning algorithm. In certain embodiments, the feedback loop further includes information from a clinical record (e.g., an EMR) of the patient. In certain embodiments, the triggered human review may update a clinical record of the patient (e.g., update the problem list of the patient).

FIG. 1 is a flowchart showing a method 100 for automatically assigning a context label to entity phrases from a clinical record, according to an illustrative embodiment. The method 100 may generally include the steps of receiving and/or accessing a clinical record of a patient (step 102); automatically identifying one or more named entity phrases (step 104); and automatically assigning a context label to each entity phrase using a reportability classifier (step 106).

Figure 2:
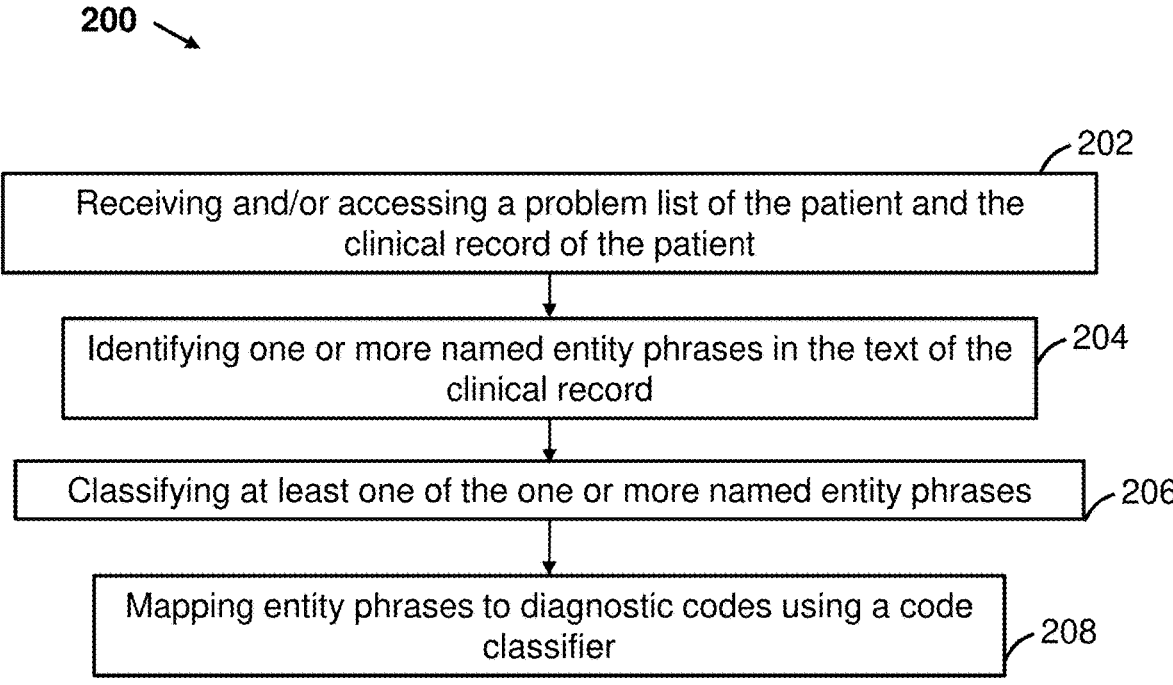
FIG. 2 is a flowchart showing a method for automatically identifying diagnostic codes using a clinical record of a patient, according to an illustrative embodiment.

FIG. 2 is a flowchart showing a method 200 for automatically identifying diagnostic codes using a clinical record of a patient, according to an illustrative embodiment. The method 200 may generally include the steps of receiving and/or accessing a problem list of the patient and the clinical record of the patient (step 202); automatically identifying one or more named entity phrases in the text of the clinical record (step 204); automatically classifying at least one of the one or more named entity phrases as reportable using a reportability classifier (step 206); and automatically mapping entity phrases to diagnostic codes using a code classifier (step 208).

FIG. 3 is a flowchart showing a method 300 of training a reportability classifier to assign a context label to a named entity phrase in a clinical record of a patient, according to an illustrative embodiment. The method 300 may generally include the steps of receiving a clinical record and a problem list and/or a billing history for a client (step 302); identifying a named entity phrase in the text of the clinical record (step 304); mapping the identified named entity phrase to a diagnosis (step 306); masking a portion of the text including the identified named entity phrase (step 308); assigning a context label to the named entity phrase using the reportability classifier based on the portion of the text with the masked named entity phrase (step 310); and comparing the assigned context label of the named entity phrase and a context label of the named entity phrase based on the problem list of the patient (step 312).

Figure 4:
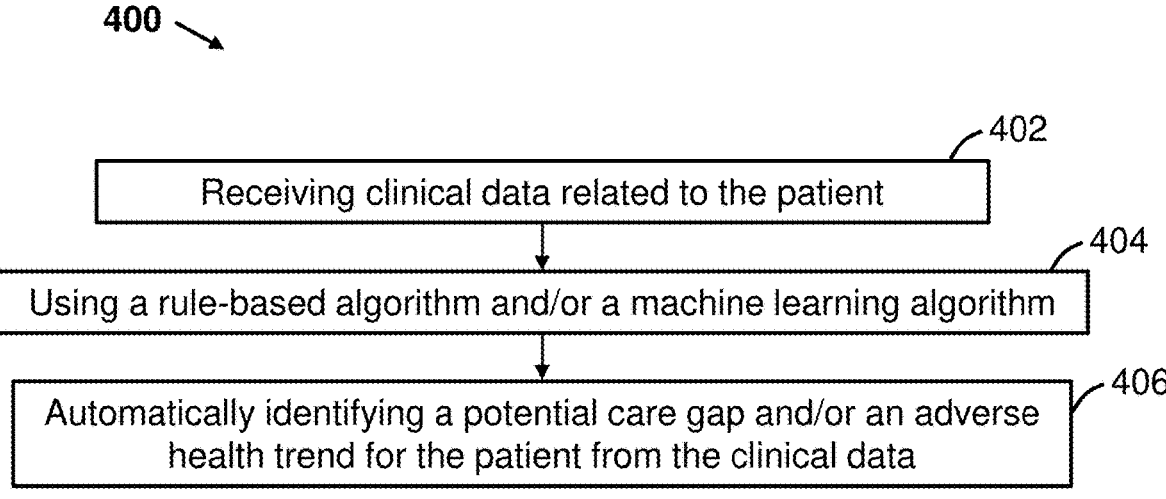
FIG. 4 is a flowchart showing a method for automatically identifying a potential care gap and/or adverse health trend for a patient, according to an illustrative embodiment.

FIG. 4 is a flowchart showing a method 400 for automatically identifying a potential care gap and/or an adverse health trend for a patient, according to an illustrative embodiment. The method 400 may generally include the steps of receiving clinical data related to the patient (step 402); using a rule-based algorithm and/or a machine learning algorithm (step 404); and automatically identifying a potential care gap and/or an adverse health trend for the patient from the clinical data (step 406).

In one example, a patient's provider narrative references a medication that indicates the patient has diabetes but the condition is missing from the electronic health record. The (human) care coordinator is presented with the finding and the relevant portion of the physician note, who communicates with the patient to confirm the correct diagnosis, provide feedback to the system, and generate a linked intervention escalating to the patient's provider to have it corrected in the medical record. The system prompts the care navigator to establish a recommended set of goals to help the patient manage their diabetes.

Another example involves determining whether a HEDIS-defined (Healthcare Effectiveness Data and Information Set) intervention applies for the patient. A HEDIS measure generally consists of a criteria applicable to a cohort of patients who, due to having a condition, should receive a specified treatment (the denominator), along with a criteria for determining whether the patient is receiving the treatment (the numerator). If the automated system determines that a patient potentially should be receiving a HEDIS defined intervention, then an insight message to the care navigator is triggered to validate this suspicion, and to escalate to the primary care physician (PCP) if appropriate. For example, there are HEDIS criteria indicating that patients who have diabetes and are male age 21-75 or female age 40-75 should receive a statin. The automated system may determine a given patient is not receiving a statin but should, based on the HEDIS criteria, and issue a notification for human review, accordingly.

Another example involves identifying a potential HCC (Hierarchical Condition Categories) gap for the patient. The system detects a reference to a more specific indication of a chronic condition (e.g., diabetes mellitus with diabetic neuropathy vs diabetes mellitus) that could increase the patient's RAF (Risk Adjustment Factor) score. The RAF score is a value that corresponds to the overall health of the patient. The RAF score may further be used to calculate a HCC score. In certain embodiments, a more specific indication corresponds to a code (e.g., an ICD code, e.g., an ICD10 code) indicative of the condition. In certain embodiments, the system identifies a plurality of codes (e.g., ICD codes), each corresponding to a different condition. In certain embodiments, the condition has not been previously identified for the patient. In certain embodiments, the identified ICD10 code(s) are used to calculate a RAF score and/or a HCC score.

The more specific indication is flagged for review by a care navigator with a suggested action plan to confirm the more specific indication with the patient. If confirmed, the patient's physician is alerted. Additionally, an appointment is scheduled to close the loop on updating the patient's medical record. The patient's physician can update their medical record based on, at least, the newly identified condition. In certain embodiments, the system includes configurations to incorporate a feedback loop and customize the thresholds surfacing (e.g., identifying) the gaps. Identification of these conditions results in the patient's physician receiving more resources (e.g., money) to manage care of the patient.

In another example, the system tracks changes in a patient's vital signs over time and can alert the patient's care navigator when vitals are changing in a way that could affect the patient's health. For example, if the system detects that a patient previously had systolic blood pressure readings that were significantly high and suddenly started trending low, the system alerts the care navigator and recommends that they ask the patient about changes to their existing blood pressure medication. If changes to the medication have occurred and are now causing symptoms of hypotension, the care navigator can generate a linked intervention escalating to the patient's provider to have the medication adjusted before the patient's blood pressure drops too low.

In another example, if the system detects a change in the medications the patient is taking and/or has been prescribed, the system alerts the care navigator so that they can confirm that the patient is aware of this change and is not confused about their instructions for taking the medication. A medication change could be a new medication being prescribed, a change in dosage of an existing medication, or the discontinuation of a medication. The system can also determine where in the physician's documentation the medication is discussed, and show this in context to the care navigator, so that they can refer to it during their conversation with the patient.

In another example, if a provider or health system has specific protocols or initiatives in place for certain cohorts of patients, the system can alert the care navigator in the event that a patient is not following the protocol or initiative. The care navigator can then use this information to generate linked interventions and goals to help the patient comply with their provider's wishes. For example, if a provider wants all obesity patients to follow a ketogenic diet, the system can identify the patients seeing that provider who also have obesity as their chronic condition and alert their care navigators to make sure the patient is following the diet plan.

In another example, if a patient is part of a remote monitoring program and the RPM (remote patient monitoring) company makes their data available, the system can monitor this data and alert the care navigator in the event of an anomalous reading.

Thus, the system integrates machine learning into patient care coordination to identify, confirm, and close care gaps and provide suggested actions for maintaining the patient's overall health. In certain embodiments, the system provides: real-time integration of natural language processing into care navigation workflows; automated identification of adverse trends and care gaps; suggested actions based on findings; tracking of goals and interventions; and end-to-end automated analysis and creation of escalations in the system of record (EMR) of the patient's primary care provider (e.g., normalization of data, bidirectional system-system integration, and the like).

Care navigators engage patients on an ongoing basis to perform condition-specific risk assessments, fill episodic care gaps, serve as care plan coaches, and remove clinical and non-clinical barriers to health.

This allows care navigators to spend time with significantly more patients, creating a more complete picture of patient health and barriers to care. Electronic health records (EHR) of patients who qualify for chronic care management (CCM) may be continuously analyzed. Actionable data insights from provider EHRs are automatically surfaced to care navigators, allowing them to focus on the most clinically important updates and intervene with the right patients at the right time. In certain embodiments, fully automated billing may be integrated with the provider EHR.

Example System Architectures

The present example is computational code corresponding to a configuration file. The configuration file is representative of an embodiment of an architecture used in systems and methods described herein. In certain embodiments, the system architecture is a two layer neural network with at least 100 (e.g., at least 150, at least 200, at least 250) nodes. In certain embodiments, the system architecture has at least two neural network layers (e.g., 3, 4, or more).

Example Configuration File

```
{
  "dataset_reader": {
    "type": "best_code",
      "objective": std.extVar("OBJECTIVE"),
      "totalLen": 256,
      "concept_level": std.extVar("CONCEPT_LEVEL")
  },
  "train_data_path": std.extVar("TRAIN_TSV_PATH"),
  "validation_data_path": std.extVar("TEST_TSV_PATH"),
  "model": {
    "type": "best_code_classifier",
      "text_field_embedder": {
        "token_embedders": {
          "tokens": {
            "type": "embedding",
```

-continued

Example Configuration File

```
      "projection_dim": 100,
      "pretrained_file": "PRE-TRAINED.TXT",
      "embedding_dim": 300,
      "trainable": false
        }
      }
  },
  "excerpt_encoder": {
    "type": "stacked_bidirectional_lstm",
    "input_size": 200,
      "num_layers": 2,
      "use_highway": true,
      "recurrent_dropout_probability": 0.3,
    #"dropout": 0.2,
    "hidden_size": 200
  },
  "classifier_feedforward": {
    "input_dim": 400,
    "num_layers": 2,
      "hidden_dims": [150,std.parseInt(std.extVar("NUM_CATS"))],
    "dropout": [0.2,0.0],
      "activations": ["relu","linear"]
  },
    "binary_feature_dim": 100
  },
  "iterator": {
    "type": "basic",
    "batch_size": 3000
  },
  "trainer": {
    "patience":20,
    "optimizer": {
      "type": "adam",
        "lr": 0.0001
    },
      "num_epochs": std.parseInt(std.extVar("NUM_EPOCHS"))
  }
}
```

Software, Computer System, and Network Environment

Certain embodiments described herein make use of computer algorithms in the form of software instructions executed by a computer processor. In certain embodiments, the software instructions include a machine learning module, also referred to herein as artificial intelligence software. As used herein, a machine learning module refers to a computer implemented process (e.g., a software function) that implements one or more specific machine learning techniques, e.g., artificial neural networks (ANNs), e.g., convolutional neural networks (CNNs), random forest, decision trees, support vector machines, and the like, in order to determine, for a given input, one or more output values. In certain embodiments, the input comprises alphanumeric data which can include numbers, words, phrases, or lengthier strings, for example. In certain embodiments, the one or more output values comprise values representing numeric values, words, phrases, or other alphanumeric strings.

For example, a machine learning module may receive as input a textual string (e.g., entered by a human user, for example) and generate various outputs. For example, the machine learning module may automatically analyze the input alphanumeric string(s) to determine output values classifying a content of the text (e.g., an intent), e.g., as in natural language understanding (NLU). In certain embodiments, a textual string is analyzed to generate and/or retrieve an output alphanumeric string. For example, a machine learning module may be (or include) natural language processing (NLP) software. Examples of NLP software include, without limitation, Long short term memory (LSTM), Bilateral LSTM (BiLSTM), Embeddings from Language Models (Elmo), Bidirectional Encoder Representations (BERT), Bert trained on clinical notes (Clinical BERT), Distilled BERT (DistilBERT), and A Lite BERT (AlBERT).

In certain embodiments, machine learning modules implementing machine learning techniques are trained, for example using datasets that include categories of data described herein. Such training may be used to determine various parameters of machine learning algorithms implemented by a machine learning module, such as weights associated with layers in neural networks. In certain embodiments, once a machine learning module is trained, e.g., to accomplish a specific task such as identifying certain response strings, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In certain embodiments, machine learning modules may receive feedback, e.g., based on user review of accuracy, and such feedback may be used as additional training data, to dynamically update the machine learning module. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of a ANN module may be carried out via specialized hardware (e.g., via an application-specific integrated circuit (ASIC)).

Figure 5:
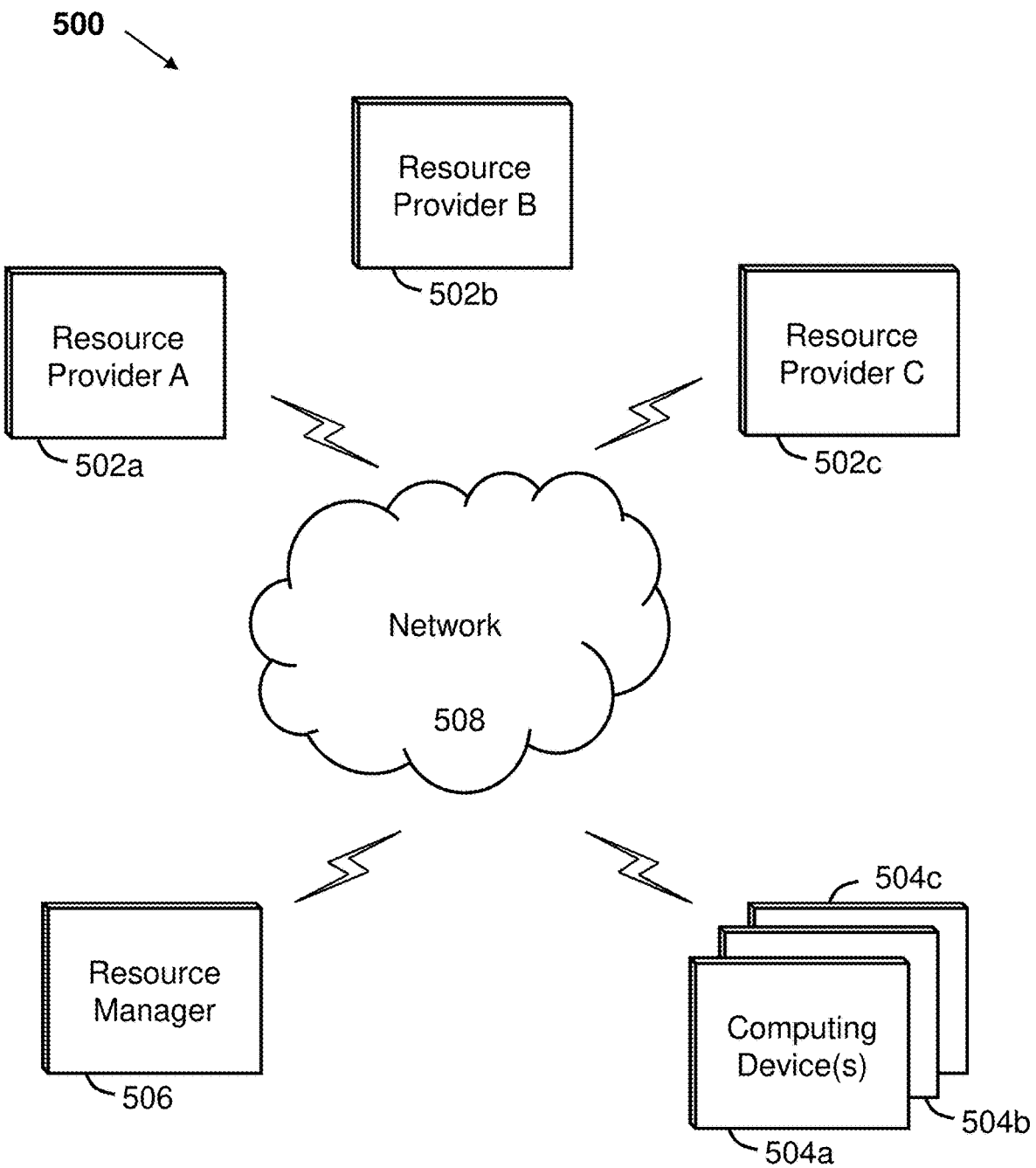
FIG. 5 is a schematic showing an implementation of a network environment for use in providing systems, methods, and architectures as described herein, according to an illustrative embodiment.

As shown in FIG. 5, an implementation of a network environment 500 for use in providing systems, methods, and architectures as described herein is shown and described. In brief overview, referring now to FIG. 5, a block diagram of an exemplary cloud computing environment 500 is shown and described. The cloud computing environment 500 may include one or more resource providers 502a, 502b, 502c (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504a, 504b, 504c (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
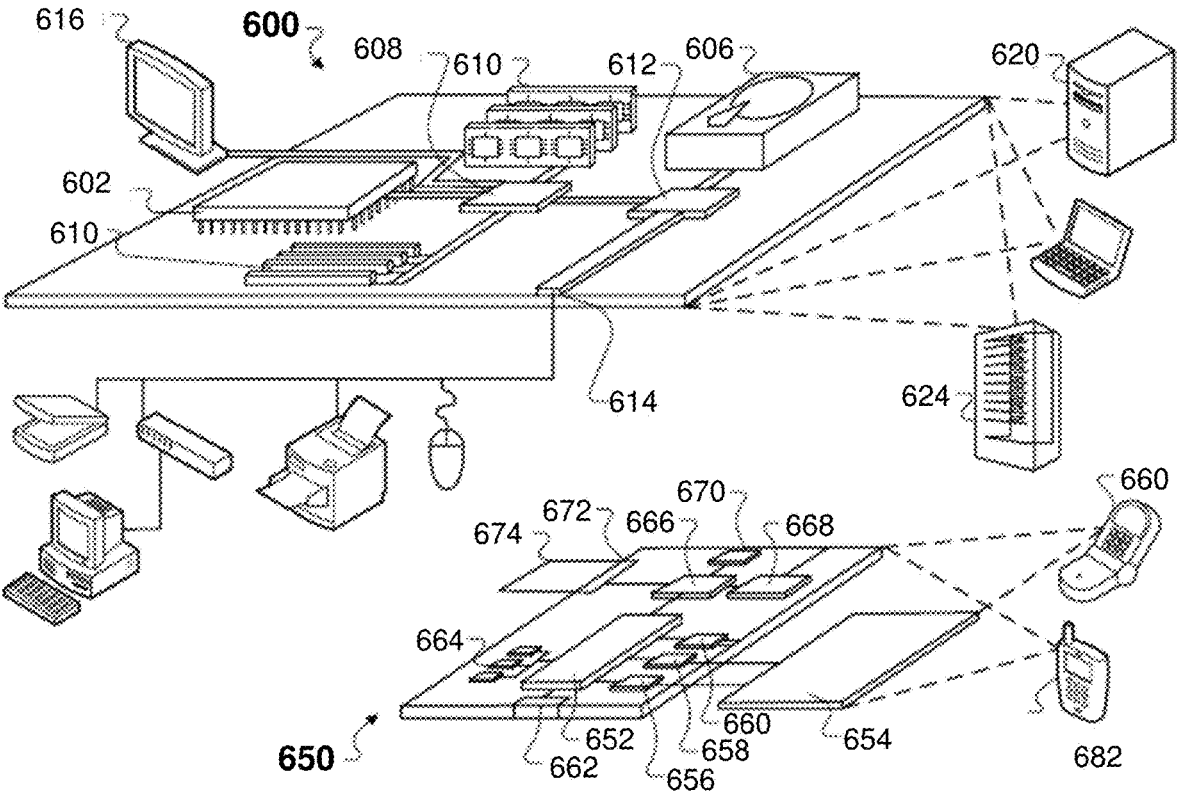
FIG. 6 is a schematic showing exemplary computing devices that can be used to implement the techniques described, according to an illustrative embodiment.

FIG. 6 shows an example of a computing device 600 and a mobile computing device 650 that can be used to implement the techniques described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 508 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 580. It may also be implemented as part of a smartphone 682, personal digital assistant, tablet, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, certain modules described herein can be separated, combined or incorporated into single or combined modules. Any modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically assigning a context label to each of one or more named entity phrases from a clinical record of a patient, the method comprising:

receiving and/or accessing, by a processor of a computing device, the clinical record of the patient and a problem list of the patient;

automatically identifying, by the processor, the one or more named entity phrases in the clinical record of the patient;

determining, via a reportability classifier, the one or more named entity phrases correspond to an International Classification of Diseases (ICD) code at least associated with a "not reportable" code or a "family history" code, wherein the reportability classifier comprises a machine learning algorithm;

automatically assigning, by the processor, the context label to each of the one or more named entity phrases corresponding to the ICD code;

automatically triggering a human review workflow based on the context label of the one or more named entity phrases;

receiving, via a control interface, feedback from a human reviewer based at least in part on the human reviewer updating a status of a problem in the problem list; and updating the machine learning algorithm of the reportability classifier using training data based at least in part on the feedback received from the human reviewer during the human review workflow, wherein the training data further comprises a weakly-labeled training dataset, wherein the reportability classifier uses distant supervision for updating the machine learning algorithm with the weakly-labeled training dataset, wherein updating the machine learning algorithm further comprises replacing the one or more named entity phrases with a mask such that the reportability classifier is forced to key off surrounding text, wherein the mask yields one or more features from the surrounding text that are used by the reportability classifier for automatically assigning the context label to the one or more named entity phrases.

2. The method of claim 1, wherein the one or more named entity phrases comprises a diagnosis, a disease, a condition, a clinical entity, or the ICD code.

3. The method of claim 1, wherein the problem list comprises a combination of one or more of: an illness, an injury, a diagnosis, a condition, and a social problem.

4. The method of claim 1, wherein the problem list comprises one or more diagnoses.

5. The method of claim 1, wherein updating the status of the problem comprises adding the problem or removing the problem in the problem list following the feedback received from the human review workflow.

6. The method of claim 5, wherein the machine learning algorithm of the reportability classifier is a deep-learning algorithm.

7. The method of claim 1, wherein the training data further comprises data from the clinical record of the patient.

8. The method of claim 1, wherein the method comprises identifying, by the processor, the problem corresponding to the patient based on the one or more named entity phrases and the context label of the one or more named entity phrases.

9. The method of claim 1, wherein the method comprises determining, by the processor, whether each of the one or more named entity phrases is a negated concept by using the reportability classifier.

10. The method of claim 1, wherein the method comprises automatically identifying a care gap using the problem list.

11. The method of claim 10, wherein automatically identifying the care gap comprises identifying a therapy and/or a treatment the patient could be receiving but is not currently receiving.

12. The method of claim 10, wherein automatically identifying the care gap comprises recommending a therapy using the problem list.

13. The method of claim 1, wherein the clinical record is an electronic medical record (EMR).

14. The method of claim 1, wherein the clinical record comprises unstructured data.

15. The method of claim 14, wherein the unstructured data comprises clinical dictation, clinical notes, and/or clinical reports.

16. The method of claim 14, wherein the unstructured data comprises one or more strings of alphanumeric characters.

17. The method of claim 1, wherein the clinical record comprises laboratory results of the patient, patient vitals, patient demographics, patient problems, patient medications, clinical notes, clinical dictation, clinical reports, and/or past medical history.

18. The method of claim 1, wherein the method does not require receiving or accessing an encounter document comprising billable codes corresponding to the patient.

19. The method of claim 1, wherein the one or more named entity phrases is a disease, a condition, or a social circumstance.

20. The method of claim 1, wherein the method comprises automatically mapping, by the processor, each of the one or more named entity phrases to a corresponding ontological code by using a first code classifier.

21. The method of claim 20, wherein the corresponding ontological code is a Unified Medical Language System (UMLS) code, the ICD code, or an RxNorm Normalized Names (RXNORM) code.

22. The method of claim 20, wherein the corresponding ontological code is a high level code that is specific to a general disease or condition.

23. The method of claim 20, wherein the method comprises updating each corresponding ontological code by using a second code classifier to make each corresponding ontological code more specific.

24. The method of claim 23, wherein the first code classifier and/or the second code classifier is/are deep-learning algorithms.

25. The method of claim 1, wherein the reportability classifier comprises a neural network.

26. The method of claim 1, wherein the reportability classifier comprises a bidirectional long short-term memory (LSTM) network.

27. The method of claim 1, wherein the reportability classifier is a trained model, having been trained using a training dataset to determine the context label of the one or more named entity phrases in medical records of one or more patients.

28. The method of claim 27, wherein the training dataset comprises one or more clinical records comprising unstructured data from each of the one or more patients, wherein each of the one or more clinical records comprises the one or more named entity phrases.

29. The method of claim 27, wherein the training dataset does not include billing codes.

30. The method of claim 27, wherein the training dataset comprises clinical dictation and/or clinical notes for each of the one or more patients.

31. The method of claim 27, wherein the training dataset comprises the problem list for each of the one or more patients.

32. The method of claim 31, wherein the reportability classifier has been trained using the training dataset by masking the one or more named entity phrases in text of the medical records and classifying an unmasked portion of the text containing the one or more named entity phrases with the context label, wherein the context label is based on, at least, a presence or an absence of the one or more named entity phrases in the problem list of the patient.

33. The method of claim 23, wherein the second code classifier is a trained model, having been trained using a code training dataset to determine a specific ontological code corresponding to the one or more named entity phrases comprising a plurality of patient examples corresponding to the specific ontological code.

34. The method of claim 33, wherein the plurality of patient examples comprises at least 10 patient examples of the specific ontological code.

35. The method of claim 33, wherein the plurality of patient examples comprises between about 10 and about 25 patient examples of the specific ontological code.

36. The method of claim 33, wherein each of the plurality of patient examples comprises a clinical dictation comprising the one or more named entity phrases.

37. The method of claim 1, wherein the method comprises automatically identifying, by the processor, one or more drugs in the clinical record of the patient.

38. The method of claim 37, wherein the method comprises mapping, by the processor, at least one of the one or more drugs to the problem.

39. The method of claim 38, wherein the method comprises updating the problem list of the patient with the problem.

40. A system for automatically assigning a context label to named entity phrases from a clinical record of a patient, the system comprising:

a processor; and a memory having instructions stored thereon, wherein the instructions, when executed by the processor, cause the processor to perform the method of claim 1.

41. The method of claim 1, wherein the reportability classifier comprises an artificial neural network (ANN) configured to process unstructured text of the clinical record.

42. The method of claim 1, wherein at least a portion of the reportability classifier is implemented on an application-specific integrated circuit (ASIC).

43. The method of claim 1, further comprising:

translating the ICD code into an appropriate "family history" ICD10 "z-code" in response to determining the one or more named entity phrases correspond to the "family history" code.

44. The method of claim 1, wherein the reportability classifier comprises Bidirectional Encoder Representations (BERT) trained on clinical notes.

45. The method of claim 1, wherein the reportability classifier comprises Bidirectional Encoder Representations (BERT).

46. The method of claim 5, wherein updating the status of the problem in the problem list further comprises identifying the problem as resolved, inactive, or active.

47. The method of claim 46, wherein updating the status of the problem in the problem list further comprises identifying the problem as improving or worsening.

48. A method for automatically identifying diagnostic codes using a clinical record of a patient, the method comprising:

receiving and/or accessing, by a processor of a computing device, a problem list of the patient and the clinical record of the patient, wherein the clinical record comprises text;

automatically identifying, by the processor, one or more named entity phrases in the text of the clinical record, thereby generating one or more identified named entity phrases;

automatically classifying, by the processor, at least one of the one or more identified named entity phrases to a diagnostic code, thereby generating a classified named entity phrase, wherein the diagnostic code is an International Classification of Diseases (ICD) code at least associated with a "not reportable" code or a "family history" code by using a reportability classifier, wherein the reportability classifier comprises a machine learning algorithm;

automatically mapping, by the processor, the classified named entity phrase to the diagnostic code by using a code classifier;

automatically triggering a human review workflow based on the diagnostic code of the classified named entity phrase;

receiving, via a control interface, feedback from a human reviewer, wherein the feedback is based at least in part on the human reviewer updating a status of a problem in the problem list; and updating the machine learning algorithm of the reportability classifier using training data based at least in part on the feedback received from the human reviewer during the human review workflow, wherein the training data further comprises a weakly-labeled training dataset, wherein the reportability classifier uses distant supervision for updating the machine learning algorithm with the weakly-labeled training dataset, wherein updating the machine learning algorithm further comprises replacing the one or more identified named entity phrases with a mask such that the reportability classifier is forced to key off surrounding text, wherein the mask yields one or more features from the surrounding text that are used by the reportability classifier for automatically classifying the at least one of the one or more identified named entity phrases.

49. A method of training a reportability classifier to assign a context label to a named entity phrase in a clinical record of a patient, the method comprising:

receiving, by a processor of a computing device, (i) the clinical record and (ii) a problem list and/or a billing history for the patient, wherein the clinical record comprises text;

identifying, by the processor, the named entity phrase in the text of the clinical record, thereby generating an identified named entity phrase;

mapping, by the processor, the identified named entity phrase to a diagnostic code, wherein the diagnostic code is an International Classification of Diseases (ICD) code at least associated with a "not reportable" code or a "family history" code, wherein the reportability classifier comprises a machine learning algorithm;

masking, by the processor, the identified named entity phrase with a mask such that the reportability classifier is forced to key off surrounding text, wherein the mask yields one or more features from the surrounding text that are used by the reportability classifier to assign the context label, thereby generating a masked portion of the text;

assigning, by the processor, the context label to the named entity phrase corresponding to the ICD code using the reportability classifier based on the masked portion of the text and the one or more features from the surrounding text, thereby generating an assigned context label;

automatically triggering, by the processor, a human review workflow based on the assigned context label of the named entity phrase;

receiving, by the processor via a control interface, feedback from a human reviewer based at least in part on the human reviewer updating a status of a problem in the problem list; and updating, by the processor, the machine learning algorithm of the reportability classifier using training data based at least in part on the feedback received from the human reviewer during the human review workflow, wherein the training data further comprises a weakly-labeled training dataset, wherein the reportability classifier uses distant supervision for updating the machine learning algorithm with the weakly-labeled training dataset, wherein the masked portion of the text is further used for updating the machine learning algorithm.

50. The method of claim 49, wherein the reportability classifier comprises a learning algorithm.

51. The method of claim 49, wherein the masked portion of the text comprises, at least, the named entity phrase.

52. The method of claim 49, wherein the reportability classifier is a neural network.

53. The method of claim 49, wherein the reportability classifier comprises a member selected from a group consisting of: Long short term memory (LSTM), Bilateral LSTM (BiLSTM), Embeddings from Language Models (Elmo), Bidirectional Encoder Representations (BERT), the BERT trained on clinical notes (Clinical BERT), Distilled BERT (DistilBERT), and A Lite BERT (ALBERT).

54. The method of claim 49, wherein the method does not require receiving an encounter document of the patient.

55. The method of claim 49, wherein the method does not require receiving one or more billable codes corresponding to a disease or a condition of the patient.

56. The method of claim 49, wherein the clinical record comprises clinical notes and/or clinical dictation.

57. The method of claim 49, wherein the clinical record comprises unstructured text.

58. The method of claim 49, wherein the context label is indicative of whether or not the named entity phrase is reportable.

59. The method of claim 49, further comprising:

translating the ICD code into an appropriate "family history" ICD10 "z-code" in response to determining the named entity phrase corresponds to the "family history" code.

60. The method of claim 49, wherein the reportability classifier comprises Bidirectional Encoder Representations (BERT) trained on clinical notes.

61. The method of claim 49, wherein the reportability classifier comprises a Long short term memory (LSTM).

62. A method for automatically identifying a potential care gap and/or a potential adverse health trend for a patient, the method comprising:

receiving and/or accessing, by a processor of a computing device, clinical data related to the patient and a problem list of the patient;

automatically identifying, by the processor, the potential care gap and/or the potential adverse health trend for the patient from the clinical data using a rule-based algorithm and a machine learning algorithm;

determining, via a reportability classifier, one or more named entity phrases correspond to an International Classification of Diseases (ICD) code at least associated with a "not reportable" code or a "family history" code, wherein the reportability classifier comprises the rule-based algorithm and the machine learning algorithm;

automatically assigning, by the processor, a context label to each of the one or more named entity phrases corresponding to the ICD code, thereby generating an assigned context label;

automatically triggering a human review workflow based on the assigned context label of the one or more named entity phrases;

receiving, via a control interface, feedback from a human reviewer based at least in part on the human reviewer updating a status of a problem in the problem list; and updating the machine learning algorithm of the reportability classifier using training data based at least in part on the feedback received from the human reviewer during the human review workflow wherein the training data further comprises a weakly-labeled training dataset, wherein the reportability classifier uses distant supervision for updating the machine learning algorithm with the weakly-labeled training dataset, wherein updating the machine learning algorithm further comprises replacing the one or more named entity phrases with a mask such that the reportability classifier is forced to key off surrounding text, wherein the mask yields one or more features from the surrounding text that are used by the reportability classifier for automatically assigning the context label to the one or more named entity phrases.

63. The method of claim 62, wherein the machine learning algorithm comprises natural language processing (NLP) software.

64. The method of claim 62, wherein the method further comprises notifying the patient of a finding of the potential care gap and/or the potential adverse health trend for the patient in response to automatically triggering the human review workflow.

65. The method of claim 62, wherein the training data further comprises data from a clinical record of the patient.

66. The method of claim 62, wherein the clinical data related to the patient comprises a healthcare provider narrative that references a medication indicating a condition that is missing from an electronic health record of the patient, thereby triggering the human review workflow.

67. The method of claim 62, wherein automatically identifying the potential care gap and/or the potential adverse health trend comprises a member selected from a group consisting of: (i) determining whether a HEDIS-defined (Healthcare Effectiveness Data and Information Set) intervention applies for the patient, (ii) tracking changes in one or more vital signs for the patient over time and alerting a care navigator for the patient of the potential adverse health trend based on the changes, (iii) identifying a change in medication prescribed and/or taken by the patient and alerting the care navigator for the patient of the change, (iv) identifying that the patient may not be following a prescribed protocol or initiative and alerting the care navigator for the patient accordingly, and (v) monitoring data from a remote monitoring program and alerting the care navigator for the patient of an anomalous reading.

68. A system for automatically identifying a potential care gap and/or adverse health trend for a patient, the system comprising:

a processor; and a memory having instructions stored thereon, wherein the instructions, when executed by the processor, cause the processor to perform the method of claim 61.

* * * * *